United States Patent [19]

Viscontini

[11] Patent Number: 4,540,783

[45] Date of Patent: Sep. 10, 1985

[54] 1',2'-DIACYL-(6R,S)-5,6,7,8-TETRAHYDRO-L-BIOPTERIN AND PROCESS FOR PREPARING THE SAME

[75] Inventor: Max Viscontini, Zurich, Switzerland

[73] Assignee: Kanegafuchi Kagaku Kogyo Kabushiki Kaisha, Osaka, Japan

[21] Appl. No.: 441,736

[22] Filed: Nov. 15, 1982

[30] Foreign Application Priority Data

Nov. 13, 1981 [JP] Japan .................................. 56-182948

[51] Int. Cl.³ .................. C07D 475/04; A61K 31/495
[52] U.S. Cl. .................................................... 544/258
[58] Field of Search ........................................ 544/258

[56] References Cited

U.S. PATENT DOCUMENTS 3,505,329  4/1970  Weinstock ........................... 544/258

OTHER PUBLICATIONS

Helvetica Chimica Acta, 60(1), pp. 211–214 (1977) by Max Viscontini et al.
Helvetica Chimica Acta, 61(7), p. 2731 (1978) by Max Viscontini et al.
Bernhard Schircks, "Neue regiospezifische Synthese von L-Biopterin und von dessen Derivaten" (Dissertation–Zurich, 1978) pp. 34–37, 69–75.

Primary Examiner—Donald G. Daus
Assistant Examiner—Robert Benson
Attorney, Agent, or Firm—Armstrong, Nikaido, Marmelstein and Kubovcik

[57] ABSTRACT

A novel compound, 1',2'-diacyl-(6R,S)-5,6,7,8-tetrahydro-L-biopterin which is prepared by catalytical hydrogenation of a 1',2'-diacyl-L-biopterin in a solvent in the presence of a catalyst. The 1',2'-diacyl-L-biopterin is prepared from a 1,1-dialkylsulfonyl-L-rhamnose through an acyl derivative of 5-deoxy-L-arabinose and a hydrazine derivative of tetrahydro-L-biopterin without isolating the intermediate products. The 1', 2'-diacyl-(6R,S)-5,6,7,8-tetrahydro-L-biopterin can be used for treatment of atypical phenylketonuria or dihydropterin-reductase deficiency* and can readily cross the blood brain barrier without neurotransmitter precursors.

6 Claims, 4 Drawing Figures

1',2'-DIACYL-(6R,S)-5,6,7,8-TETRAHYDRO-L-BIOPTERIN AND PROCESS FOR PREPARING THE SAME

BACKGROUND OF THE INVENTION

The present invention relates to a novel compound, 1',2'-diacyl-(6R,S)-5,6,7,8-tetrahydro-L-biopterin and a novel compound, 1',2'-diacyl-L-biopterin, and processes for preparing them.

It has been found recently that (6R,S)-5,6,7,8-tetrahydro-L-biopterin and 7,8-dihydro-L-biopterin can be successfully used for a treatment of patients with atypical phenylketonuria (hereinafter referred to as PKU) or with dihydropterin-reductase deficiency [A. B. Schircks, M. Viscontini and J. Schaub, Lancet, 1979, 131; H.-Ch. Curtius, A. Niederwieser, M. Viscontini, A. Otten, J. Schaub, S. Scheibenreiter and H. Schmidt, Clin. Chim. Acta, 93, 251 (1979)].

Though both compounds can conduct an enzymatic hydroxylation of L-tryptophane and L-tyrosine to 5-hydroxytryptophane and DOPA, respectively, in the brain, they have difficulties to cross the blood brain barrier. Therefore neurotransmitter precursors must be given with those compounds during the treatment of both deficiency-diseases.

The present invention has been completed on the basis of the fact that lipophile substances can more readily cross the brain barrier than compounds which possess a greater polarity as (6R,S)-tetrahydro-L-biopterin with its amphoteric nucleus and its free sugar chain.

An object of the present invention is to provide a novel compound, 1',2'-diacyl-(6R,S)-5,6,7,8-tetrahydro-L-biopterin having a low polarity and the same effect as (6R,S)-5,6,7,8-tetrahydro-L-biopterin in treatment of atypical PKU and dihydropterin-reductase deficiency without neurotransmitter precursors.

Another object of the invention is to provide a process for preparing the compound by acylating the free hydroxy groups of the side chain of (6R,S)-tetrahydro-L-biopterin.

SUMMARY OF THE INVENTION

In accordance with the present invention, there is provided a novel compound, 1',2'-diacyl-(6R,S)-5,6,7,8-tetrahydro-L-biopterin having the general formula (I):

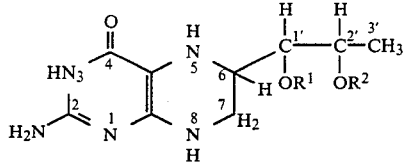

wherein $R^1$ and $R^2$ are the same or different and each is an acyl group.

In accordance with the present invention, there is also provided a process for preparing the compound of the general formula (I) by catalytically hydrogenating a 1',2'-diacyl-L-biopterin having the general formula (II):

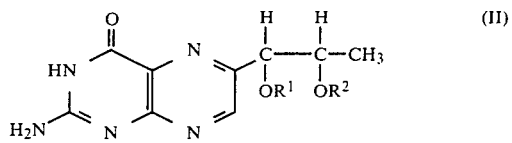

wherein $R^1$ and $R^2$ are as defined above, in a solvent in the presence of a catalyst.

Furthermore, there is provided a novel compound, 1',2'-diacyl-L-biopterin having the general formula (III):

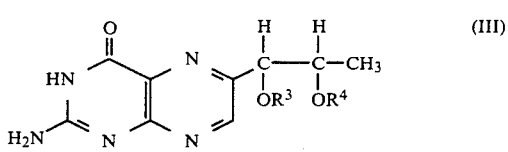

wherein $R^3$ and $R^4$ are the same or different and each is an acyl group having 3 or more carbon atoms.

1',2'-diacyl-L-biopterin of the general formula (III) can be prepared by converting L-rhamnose to an acyl derivative of 5-deoxy-L-arabinose-phenylhydrazone through a 1,1-dialkylsulfonyl-L-rhamnose, reacting the obtained acyl derivative with 2,4,5-triamino-6-hydroxy-pyrimidine to obtain a hydrazine derivative of tetrahydro-L-biopterin and oxidizing the hydrazine derivative, without isolating the intermediate products in the course of reaction from the 1,1-dialkylsufonyl-L-rhamnose to the 1',2'-diacyl-L-biopterin.

The compound having the general formula (I) can be used for treatment of atypical PKU or dihydropterin-reductase deficiency and can readily cross the blood brain barrier without neurotransmitter precursors.

DETAILED EXPLANATION

Figure 1:
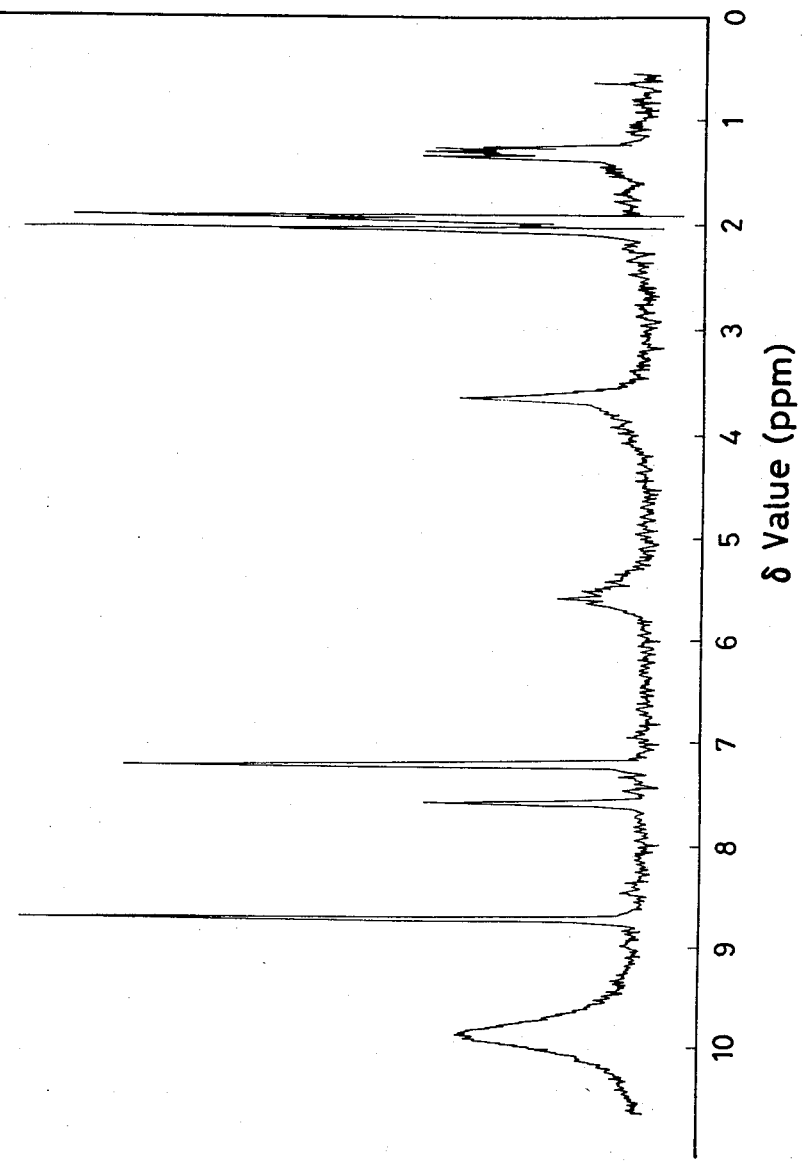
FIG. 1 and FIG. 2 represent, respectively, $^1$H-NMR-spectrum chart and $^{13}$C-NMR-spectrum chart of 1',2'-diacetyl-(6R,S)-5,6,7,8-tetrahydro-L-biopterin.

The acyl groups represented by $R^1$ and $R^2$ in the general formulas (I) and (II) are protective groups of the hydroxyl groups of (6R,S)-5,6,7,8-tetrahydro-L-biopterin.

The acyl group has preferably 1 to 10 carbon atoms, in particular 3 to 10 carbon atoms. Preferable acyl group is represented by the general formula $R^5CO$— wherein $R^5$ is hydrogen or a hydrocarbon residue having 1 or more carbon atoms, in particular 2 to 9 carbon atoms. Preferable examples of the hydrocarbon residue represented by $R^5$ are, for instance, a linear or branched alkyl group having 1 or more carbon atoms, preferably 2 to 9 carbon atoms, which is either saturated or unsaturated; a substituted or unsubstituted phenyl group represented by the general formula

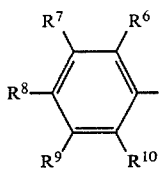

wherein $R^6$, $R^7$, $R^8$, $R^9$ and $R^{10}$ are hydrogen or a linear or branched alkyl group wherein the combined number of carbon atoms is $R^6$, $R^7$, $R^8$, $R^9$, $R^{10}$ is preferably not more than 3; a substituted or unsubstituted benzyl group represented by the general formula

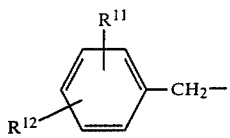

wherein $R^{11}$ and $R^{12}$ are hydrogen, methyl or ethyl wherein the combined number of carbon atoms $R^{11}$ and $R^{12}$ is preferably not more than 2; and a substituted or unsubstituted arylalkyl group represented by the general formula

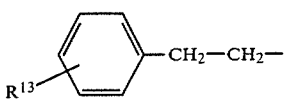

wherein $R^{13}$ is hydrogen or methyl group. Among the above acyl groups, formyl, acetyl, propionyl, butyryl, isobutyryl, valeryl, isovaleryl and benzoyl are most preferable. It is preferable that $R^1$ and $R^2$ are the same.

The compound of the general formula (I) has two diastereomers, i.e. 1',2'-diacyl-(6R)-5,6,7,8-tetrahydro-L-biopterin and 1',2'-diacyl-(6S)-5,6,7,8-tetrahydro-L-biopterin which are diastereomeric at the 6 position. The compound of the present invention includes the two diastereomers and a mixture thereof.

The compound of the present invention can be readily prepared by means of catalytic hydrogenation of the compound of the general formula (II) in a suitable solvent in the presence of a catalyst.

Examples of the catalyst are, for instance, Pt, Ni, Cr, Pd, Rh, and the like.

Examples of the solvent are, for instance, a solvent in which the compound (II) is soluble, such as trifluoroacetic acid, methanol, ethanol, propanol (1) and propanol (2), a conc. HCl, an acidic water, a basic water, or the like and a solvent in which the compound (II) is insoluble, but the compound (I) is soluble, such as acetic acid.

When the solvent which dissolves the compound (II) is employed, the process of the present invention can be carried out in a similar manner to the known process for preparing tetrahydro-L-biopterin by hydrogenating L-biopterin in trifluoroacetic acid in the presence of Pt [Bernard Schircks, Jost H. Bieri and Max Viscontini, Helvetica Chimica Acta, 61(7), 2731 (1978)].

In case where the compound (I) is used as an active ingredient of a pharmaceutical composition, it is not preferable that any solvent which is not pharmacologically acceptable remains. In such view point, the employment of acetic acid as a solvent is practically useful.

The catalytical hydrogenation of L-biopterin can also be carried out by using acetic acid as a solvent.

As a result of the catalytical hydrogenation, a mixture of 1',2'-diacyl-(6R)-5,6,7,8-tetrahydro-L-biopterin and 1',2'-diacyl-(6S)-5,6,7,8-tetrahydro-L-biopterin is, in general, obtained in a proportion of about 1:1. The mixture can be resolved, for example, by means of high pressure liquid chromatography which is adapted to a resolution of (6R,S)-tetrahydro-L-biopterin [J. Biol. Chem., 253, 1593 (1978)].

The compound (II) can be prepared by a similar process to the process for preparing 1',2'-diacetyl-L-biopterin [Bernard Schircks, Jost H. Bieri and Max Viscontini, Helvetica Chimica Acta, 60(1), 211 (1977)]. According to the process, L-rhamnose hydrate is reacted with ethanethiol. The obtained L-rhamnose-diethylmer-captal is converted to 5-deoxy-L-arabinose through 1,1-diethylsulfonyl-L-rhamnose. 5-Deoxy-L-arabinose is reacted with phenylhydrazine to obtain 5-deoxy-L-arabinose-phenylhydrazone. 5-Deoxy-L-arabinose-phenyl-hydrazone is reacted with an acylating agent. The obtained 2,3,4-triacyl-5-deoxy-L-arabinose-phenylhyrazone is reacted with 2,4,5-triamino-6-hydroxy-pyrimidine dihydrochloride, and then oxidized with an oxidizing agent such as iodine to obtain a 1',2'-diacyl-L-biopterin. L-Biopterin can be obtained by deacylation of the 1',2'-diacyl-L-biopterin.

The above-mentioned process, however, is not suitable for industrial processes because large amount of solvent is required and the total yield of 1',2'-diacyl-L-biopterin is low due to its complicated procedures.

The inventor has found the fact that when the the course of reaction from the 1,1-dialkylsulfonyl-L-rhamnose to the 1',2'-diacyl-L-biopterin, if necessary, to L-biopterin is carried out without isolating the intermediate products, that is to say, in one pot synthesis, it is possible to improve the total yield, to reduce the amount of the solvent and to simplify the procedures. The improved process of the present invention is quite suitable for industrial processes. As a mercaptal, methylmercaptal and propanethiol may be employed in addition to ethanthiol. In case of employing methylmer-captal and propanethiol, the respective starting compound of the improved process is 1,1-dimethylsulfonyl-L-rhamnose and 1,1-dipropylsulfonyl-L-rhamnose.

The improved process of the present invention can also be adapted to a production of L-biopterin and to productions of monapterins and neopterins which have different side chains at the 6 position.

Among the compounds (II), the 1',2'-diacyl-L-biopterin having the general formula (III), that is to say, the acyl group of which has 3 or more carbon atoms is a novel compound.

The compound (I) of the present invention can be isolated from a reaction mixture in a form of an inorganic salt such as a hydrochloride, a sulfate or a phosphate, an organic salt such as an acetate, an oxalte, or a complex salt.

The present invention is more specifically described and explained by means of the following Examples. It is to be understood that the present invention is not limited to the Examples and various changes and modifications may be made in the invention.

EXAMPLE 1

Preparation of 1',2'-diacetyl-(6R,S)-5,6,7,8-tetrahydro-L-biopterin

After reducing 350 mg. of PtO$_2$ by a usual method with H$_2$ in 50 ml. of trifluoroacetic acid, 1 g. of pure 1',2'-diacetyl-L-biopterin was added to the obtained suspension. Then, H$_2$ was passed into the suspension. After 40 min. the rate of H$_2$-uptake was slowed down, and the H$_2$-uptake was stopped after 45 min. The catalyst was quickly filtered and a colorless filtrate was frozen in liquid N$_2$. A cold mixture of 20 ml. of ether was added thereto. While melting the frozen solution at room temperature, 1',2'-diacetyl-(6R,S)-5,6,7,8-tetrahydro-L-biopterin·2HCl was separated as a white powder. The powder was centrifuged, washed with acetonitrile and ether, dried over KOH in desiccator, and then dried under reduced pressure (0.01 Torr) at 60° C. for 15 hours. Yield: 1.1 g.

The obtained 1',2'-diacetyl-(6R,S)-5,6,7,8-tetrahydro-L-biopterin was analysed by means of $^1$H-NMR (d$_5$-pyridine) and $^{13}$C-NMR (D$_2$O).

Figure 2:
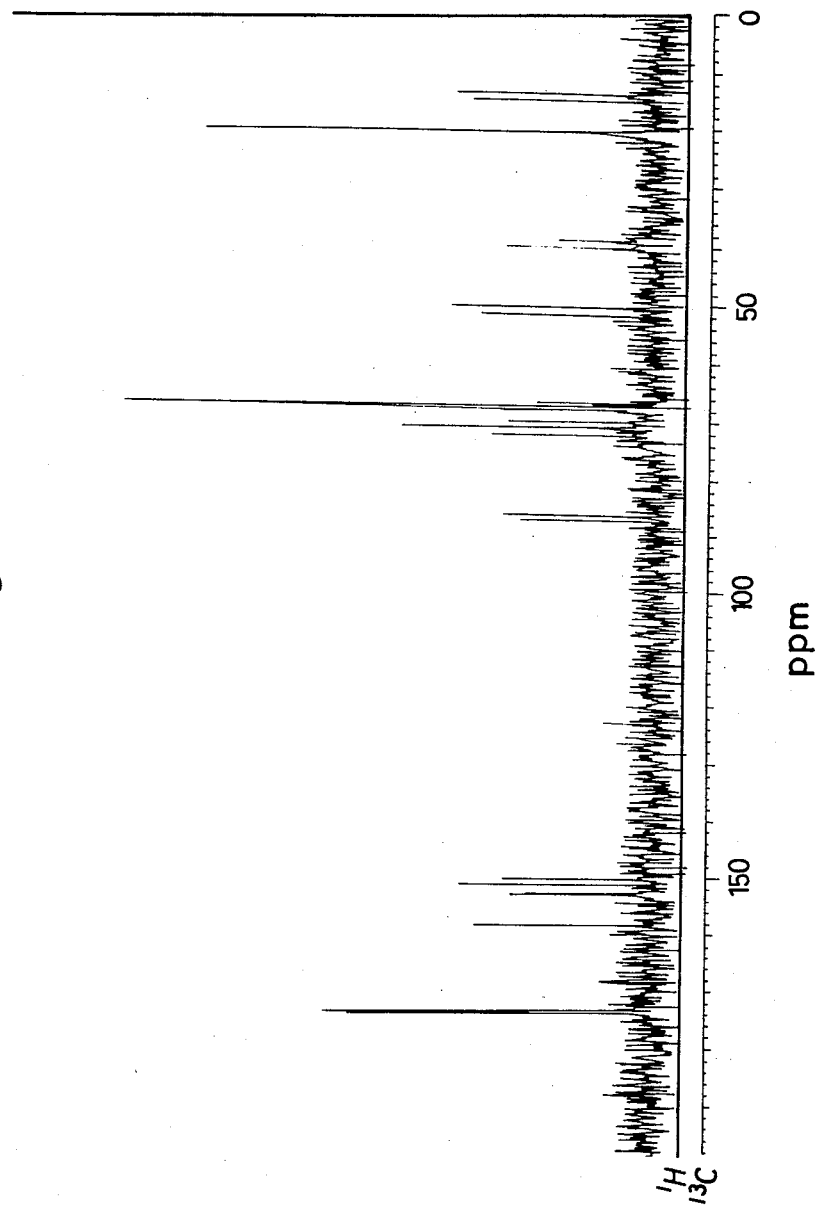

The $^1$H-NMR-spectrum charts are shown in FIG. 1 and FIG. 2.

FIG. 1 and FIG. 2 showed distinctly that the obtained compound was a diastereomeric mixture of 1',2'-diacetyl-(6R)-5,6,7,8-tetrahydro-L-biopterin and 1',2'-diacetyl-(6S)-5,6,7,8-tetrahydro-L-biopterin in a proportion of about 1:1.

EXAMPLE 2

Preparation of (6R,S)-5,6,7,8-tetrahydro-L-biopterin 10 mg. of PtO$_2$ were stirred with 30 ml. of pure acetic acid at room temperature in the atmosphere of hydrogen for about 10 minutes until the catalyst was completely reduced and saturated with hydrogen. 500 mg. of pure L-biopterin were then added. The L-biopterin was not soluble in acetic acid and a suspension was obtained. It was stirred in the atmosphere of hydrogen until all the L-biopterin became into solution. It took about 5 hours. The obtained solution was then filtered from the catalyst and the filtrate was cooled in a freezing mixture until it solidified. Then a solution of 9 ml. of methanol, 90 ml. of ether and 1 ml. of 12 N HCl was added to the solidified mixture and the whole flask was allowed to come to room temperature. The precipitated insoluble tetrahydrobiopterin·2HCl was filtered and washed with ethanol and then ether until became free from excess HCl and dried under reduced pressure. The crude tetrahydrobiopterin was crystallized with acetic acid. For the elimination of both solvents it was further dried in vacuo (0.01 Torr) at 60° C. for 16 hours. Yield: about quantitative.

The following Table 1 shows the different times which are required for the complete catalytic reduction of L-biopterin by using several varieties of amount of biopterin, catalyst or acetic acid.

TABLE 1

| Amount of biopterin (mg.) | Amount of catalyst (mg.) | Amount of solvent (Acetic acid) (ml.) | Time for complete reduction (hours) |
| --- | --- | --- | --- |
| 100 | 40 | 6 | 1.5 |
| 100 | 20 | 6 | 1.5 |
| 100 | 10 | 6 | 2.0 |
| 200 | 10 | 12 | 3.0 |
| 300 | 10 | 18 | 4.0 |
| 400 | 10 | 24 | 4.5 |
| 500 | 10 | 30 | 5.0 |
| 1000 | 20 | 60 | 8.0 |

EXAMPLE 3

Preparation of 1',2'-dibutyryl-(6R,S)-5,6,7,8-tetrahydro-L-biopterin 50 mg. of PtO$_2$ were stirred with pure 25 ml. of acetic acid at room temperature in the atmosphere of hydrogen for about 10 minutes until the catalyst was completely reduced and saturated with hydrogen. 500 mg. of 1',2'-dibutyryl-L-biopterin were added. Dibutyryl-L-biopterin was not soluble in acetic acid and a suspension was obtained. It became a solution while a tetrahydro-derivative was produced by means of hydrogenation with stirring. The clear solution was obtained after 5 hours. The obtained solution was filtered from the catalyst and cooled in a freezing mixture (ice and salt). After freezing, a solution of 1 ml. of 12 N HCl, 9 ml. of methanol and 300 ml. of ether was added and the whole flask was allowed to come to room temperature. The insoluble dibutyryl-tetrahydro-L-biopterin·2HCl was filtered, washed with ethanol and then ether until became free from HCl and dried in vacuo (0.01 Torr) at 60° C. for 16 hours for the elimination of the solvents. Yield: about quantitative.

The obtained 1',2'-dibutyryl-(6R,S)-5,6,7,8-tetrahydro-L-biopterin was analyzed by means of $^1$H-NMR (1 N DCl).

Figure 3:
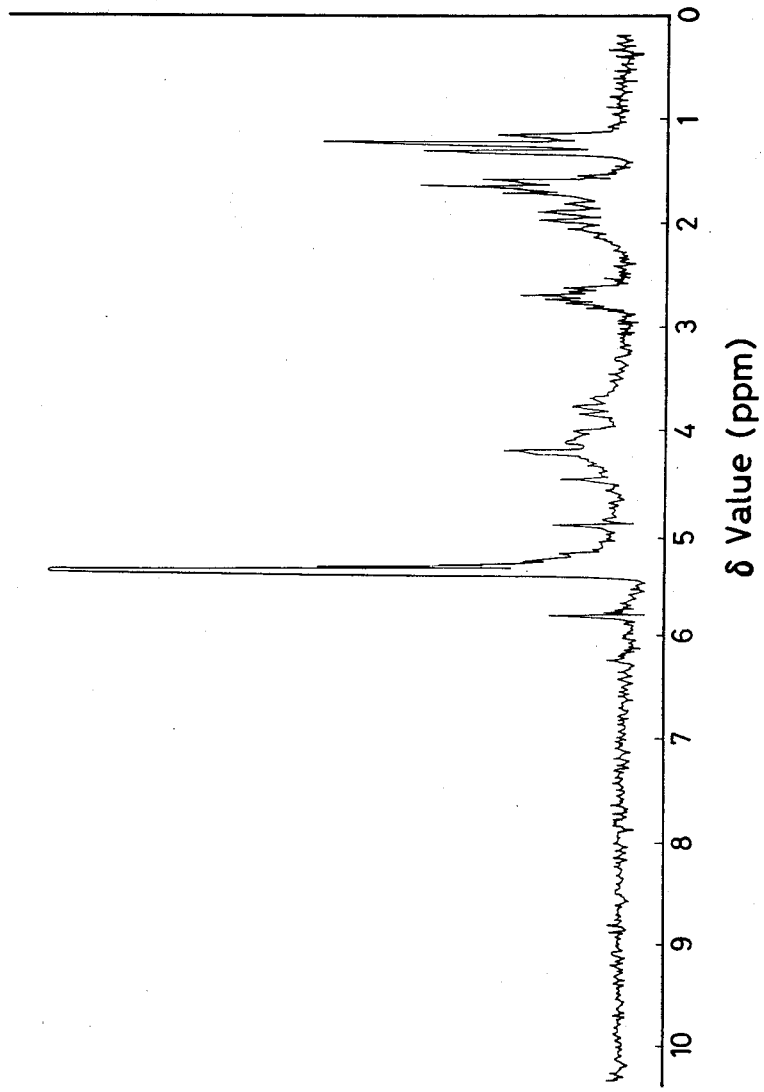
FIG. 3 represents $^1$H-NMR-spectrum chart of 1',2'-dibutyryl-(6R,S)-5,6,7,8-tetrahydro-L-biopterin.

The $^1$H-NMR-spectrum cart is shown in FIG. 3: $^1$H-NMR-spectrum analysis (the values of the chemical shifts are expressed in δ): (recorded in CDCl$_3$).

4.33-366 (m, H$_2$—C (7), H—C (6); H—C (1'); H—C (2')); 2.66 (m, 2×H$_2$C—(CH$_2$—CH$_3$)); 1.90 (m, 2×H$_2$C—(CH$_3$)); 1.60 (m, H$_3$—C (3')); 1.20 (t, H$_3$—C—(CH$_2$)).

FIG. 3 shows distinctly that the obtained compound was a diastereomeric mixture of 1',2'-dibutyryl-(6R)-5',6',7',8'-tetrahydro-L-biopterin and 1',2'-dibutyryl-(6S)-5',6',7',8'-tetrahydro-L-biopterin in a proportion of about 1:1.

EXAMPLE 4

One pot synthesis of 1',2'-dibutyryl-L-biopterin

A suspension of 14 g. (42.1 mmol.) of diethylsulfonyl-L-rhamnose in 120 ml. of water was treated with 4 N NH$_4$OH while stirring until the pH of the solution became 9 to 10. After 14 hours standing with stirring from time to time, the precipitate of diethylsulfonyl-methane was filtered off and the filtrate was dried in vacuo at 40° C. The residue was dissolved in 80 ml. of absolute methanol. After adding 5 g. (46 mmol.) of pure phenylhydrazine, the solution was kept at room temperature for 1 hour and then dried in vacuo at 40° C. The residue was washed two or three times with ether (50 ml. each time) and dried. The dried residue was dissolved in 35 ml. of pyridine and the solution was cooled. To the ice-cold solution of 0°–5° C. 35 ml. of butyric anhydride were slowly added. After adding completely, the reaction mixture was allowed to stand in the ice-bath for 10 min. and then it was kept at room temperature for 5 hours.

After 200 ml. of methanol were added to the solution, the solution was kept at room temperature for 10–15 hours (overnight). A solution of 1.0 g. of sodium dithionite ($Na_2S_2O_4$) and 12.5 g. of sodium acetate·$3H_2O$ dissolved in 300 ml. of water, and a suspension of 12.0 g. of 6-hydroxy-2,4,5-triamino-pyrimidine sulfate·$H_2O$ in 500 ml. of water were then added successively to the methanol/pyridine solution. The whole reaction mixture was closed under nitrogen and stirred at 35°–40° C. for 20 hours to give an homogeneous, reddish brown solution. In the resulting solution the obtained tetrahydrobiopterin derivative was oxidized by adding 25 g. of iodine dissolved in 300 ml. of methanol. The excess of iodine, if any, was removed with sodium thiosulfate. If no excess was present, a small quantity of iodine solution was added in order to complete the oxidation of the tetrahydrobiopterin derivative. During the oxidation a fine brown crystalline precipitate was obtained.

The resulting oxidized suspension was concentrated to 50 ml. in vacuo at 40° C. and filtered. The insoluble fraction was washed with water, 40 ml. of cold ethanol and finally with ether. The residue was then recrystallized from hot ethanol with active charcoal and the crystal was filtered while heating.

After cooling, yellowish precipitate of 1′,2′-dibutyryl-L-biopterin was obtained in the filtrate. It was filtered, washed with ether and dried to give 10.3 g. of 1′,2′-dibutyryl-L-biopterin. Yield: 65%.

Figure 4:
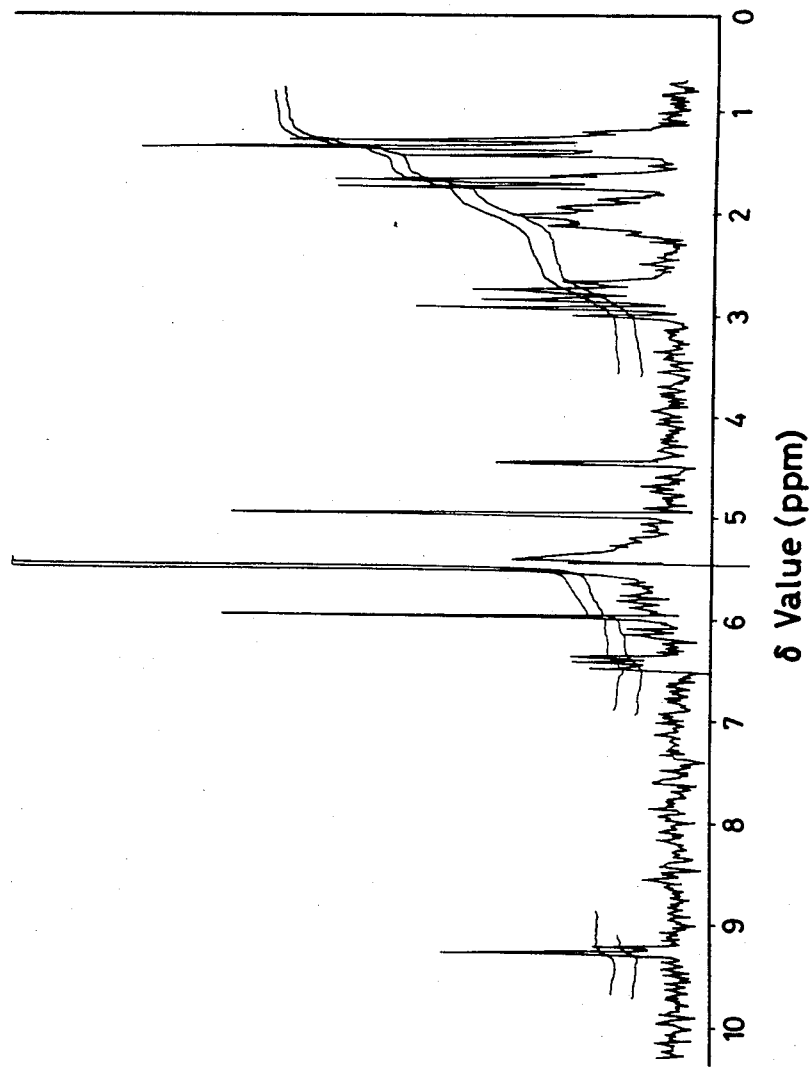
FIG. 4 represents $^1$H-NMR-spectrum chart of 1',2'-dibutyryl-L-biopterin.

The obtained 1′,2′-dibutyryl-L-biopterin was analyzed by means of several analytical methods. The $^1H$-NMR-spectrum chart is shown in FIG. 4.

Rf (3% $NH_4Cl/H_2O$, on cellulose)=0.36 $[\alpha]_{589}^{220}$=-74.3±3° (C=0.8, 1 N HCl)

The optical rotation increased with the time, perhaps because the butyrate ester is hydrolyzed in an acidic solution. $^1$H-NMR-spectrum analysis (δ: p.p.m.): (90 MHz, in DCl) 9.33 (s, H—C (7); 6.5 (d, H—C (1′)); 5–6 (m, $H_2O$, H—C (2′)); 3–2.66 (m, 2×$H_2C$—($CH_2$—($C$-$H_3$)); 2.30–1.8 (m, 2×$H_2C$—($CH_3$)); 1.66 (d, $H_3$—C (3′)); 1.33 (t, $H_3C$—($CH_2$)).

Elemental analysis for $C_{17}H_{23}N_5O_5$
Calc. (%): C 54.11, H 6.1, N 18.56.
Found. (%): C 54.09, H 6.99, N 18.99

EXAMPLE 5

One pot synthesis of 1′,2′-diacetyl-L-biopterin

A suspension of 14 g. (42.1 mmol.) of diethylsulfonyl-L-rhamnose in 120 ml. of water was treated with 4 N $NH_4OH$ while stirring until the pH of the solution reached 9 to 10. After 14 hours-standing with stirring from time to time, the precipitate of diethylsulfonyl-methane was filtered off and the filtrate was dried in vacuo at 40° C. The residue was dissolved in 80 ml. of absolute methanol. After adding 5 g. (46 mmol.) of pure phenylhydrazine, the solution was kept at room temperature for 1 hour and then dried in vacuo at 40° C. The residue was washed two or three times with ether (50 ml. each time) and dried. The dried residue was dissolved in 35 ml. of pyridine and the solution was cooled. To the cooled solution of 0°–5° C. 35 ml. of acetic anhydride were slowly added. After adding completely, the reaction mixture was allowed to stand in the ice-bath for 10 min. and then it was kept at room temperature for 5 hours. After 200 ml. of methanol were added to the solution, the solution was kept at room temperature for 10–15 hours (overnight). A solution of 1.0 g. of sodium dithionite ($Na_2S_2O_4$) and 12.5 g. of sodium acetate·$3H_2O$ dissolved in 300 ml. of water, and a suspension of 12.0 g. of 6-hydroxy-2,4,5-triamino-pyrimidine-sulfate·$H_2O$ in 500 ml. of water were then added successively to the methanol/pyridine solution. The whole reaction mixture was closed under nitrogen and stirred at 35°–40° C. for 20 hours to give an homogeneous, reddish brown solution. In the resulting solution the obtained tetrahydrobiopterin derivative was oxidized by adding 25 g. of iodine dissolved in 300 ml. of methanol. The excess of iodine, if any, was removed with sodium thiosulfate. If no excess was present, a small quantity of iodine solution was added in order to complete the oxidation of the tetrahydrobiopterin derivative. During the oxidation a fine brown crystalline precipitate was obtained.

The resulting oxidized solution was then concentrated to about 100 ml. and filtered after cooling in the refrigerator for some hours. The filtered crude diacetyl-biopterin was washed with 50 ml. of cold water, 100 ml. of cold ethanol, 100 ml. of ether and dried. The dried residue was dissolved in about 1200 ml. of boiling water and discolored with about 0.5 g. of active charcoal. The solution was filtered while heating, the charcoal bed was washed with 50 ml. of boiling water, the filtrate was allowed to cool to room temperature and then kept to 0°–5° C. for 10 hours.

The crystalline diacetyl-L-biopterin was filtered, washed twice with 50 ml. of ethanol, then ether and dried to give 8.1 g. of crystalline 1′,2′-diacetyl-L-biopterin. Yield: 60%.

EXAMPLE 6

One pot synthesis of L-biopterin

A suspension of 14 g. (42.1 mmol.) diethyl-sulfonyl-L-rhamnose in 120 ml. of water was treated with 4 N $NH_4OH$ while stirring until the pH of the solution reached 9 to 10. After 14 hours standing with stirring from time to time, the precipitate of diethylsulfonyl-methane was filtered off and the filtrate was dried in vacuo at 40° C. The residue was dissolved in 80 ml. of absolute methanol. After adding 5 g. (46 mmol.) of pure phenylhydrazine, the solution was kept at room temperature for 1 hour and then dried in vacuo at 40° C. The residue was washed two or three times with ether (50 ml. each time) and dried. The dried residue was dissolved in 35 ml. of pyridine and the solution was cooled. To the ice-cooled solution of 0°–5° C. 35 ml. of acetic anhydride were slowly added. After adding completely, the reaction mixture was allowed to stand in the ice-bath for 10 min. and then it was kept at room temperature for 5 hours. After 200 ml. of methanol were added to the solution, the solution was kept at room temperature for 10–15 hours (overnight). A solution of 1.0 g. of sodium dithionite ($Na_2S_2O_4$) and 12.5 g. of sodium acetate·$3H_2O$ dissolved in 300 ml. of water, and a suspension of 12.0 g. of 6-hydroxy-2,4,5-triamino-pyrimidine-sulfate $H_2O$ in 500 ml. of water were then added sucessively to the methanol/pyridine solution. The whole reaction mixture was closed under nitrogen and stirred at 35°–40° C. for 20 hours to give an homogeneous, reddish brown solution. In the resulting solution the obtained tetrahydrobiopterin derivative was oxidized by adding 25 g. of iodine dissolved in 300 ml. of methanol. The excess of iodine, if any, was removed with sodium thiosulfate. If no excess was present, a small quantity of iodine solution was added in order to complete the oxidation of the tetrahydrobiopterin derivative. During the oxidation a fine brown crystalline precipitate was obtained.

The resulting oxidized solution was concentrated in vacuo to about 100 ml. 150 ml. of ethanol and 250 ml. of 14 N NH₄OH were added to the concentrate. The resulting mixture was kept at 50° C. for one hour. The deacetylated biopterin solution was then evaporated to dryness in vacuo at 40° C., the residue was taken up with 100 ml. of methanol and filtered.

The crude biopterin was washed with 50 ml. of cold water and 200 ml. of ethanol. And then, without drying, it was dissolved in 1400 ml. of boiling water with the smallest quantity of active charcoal to discolorize it. After hot filtration, the solution was allowed to cool to room temperature and then kept at 5° C. for 10 hours. The crystalline biopterin was filtered, washed with cold water, ethanol, ether and then dried in vacuo (0.01 Torr) at 40° C. for 14 hours until became free from solvents to give 6 g. of L-biopterin. Yield: 60%.

What is claimed is:

1. A 1',2'-diacyl-6(R,S)-5,6,7,8-tetrahydro-L-biopterin of the formula (I):

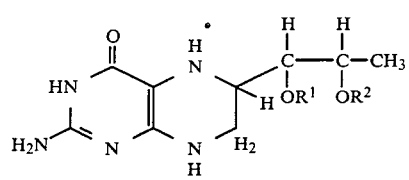

wherein R1 and R2 are the same or different and each is an acyl group having 1 to 10 carbon atoms represented by $R^5CO$—in which $R^5$ is hydrogen; a linear or branched alkyl group having 1 to 9 carbon atoms; an alkyl substituted or unsubstituted phenyl group having 6 to 9 carbon atoms; a methyl, dimethyl or ethyl substituted or unsubstituted benzyl group; or a methyl substituted or unsubstituted phenyl ethyl group.

2. The compound of claim 1, wherein $R^1$ and $R^2$ are the same acyl group.

3. The compound of claim 1, or 2, wherein said acyl group is a member selected from the group consisting of formyl, acetyl, propionyl, butyryl, isobutyryl, valeryl and benzoyl.

4. A 1',2'-diacyl-6(R)-5,6,7,8-tetrahydro-L-biopterin of the formula (I):

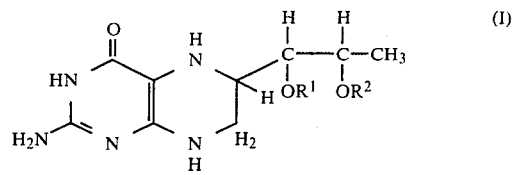

wherein R1 and R2 are the same or different and each is an acyl group having 1 to 10 carbon atoms represented by $R^5CO$—in which $R^5$ is hydrogen; a linear or branched alkyl group having 1 to 9 carbon atoms; an alkyl substituted or unsubstituted phenyl group having 6 to 9 carbon atoms; a methyl, dimethyl or ethyl substituted or unsubstituted benzyl group; or a methyl substituted or unsubstituted phenyl ethyl group.

5. A 1',2'-diacyl-6(S)-5,6,7,8-tetrahydro-L-biopterin of the formula (I):

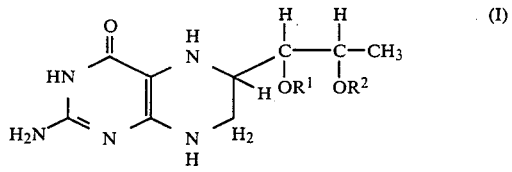

wherein R1 and R2 are the same or different and each is an acyl group having 1 to 10 carbon atoms represented by $R^5CO$—in which $R^5$ is hydrogen; a linear or branched alkyl group having 1 to 9 carbon atoms; an alkyl substituted or unsubstituted phenyl group having 6 to 9 carbon atoms; a methyl, dimethyl or ethyl substituted or unsubstituted benzyl group; or a methyl substituted or unsubstituted phenyl ethyl group.

6. The compound of claim 1, which is a mixture of a 1',2'-diacyl-(6R)-5,6,7,8-tetrahydro-L-biopterin and a 1',2'-diacyl-(6S)-5,6,7,8-tetrahydro-L-biopterin in a proportion of about 1:1.

* * * * *